(12) United States Patent
Kinoshita et al.

(10) Patent No.: US 7,088,514 B2
(45) Date of Patent: Aug. 8, 2006

(54) PARTICLE SIZE VARIABLE REACTOR

(75) Inventors: Takatoshi Kinoshita, Aichi (JP); Shintaro Washizu, Shizuoka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 11/245,150

(22) Filed: Oct. 7, 2005

(65) Prior Publication Data

US 2006/0035266 A1 Feb. 16, 2006

Related U.S. Application Data

(62) Division of application No. 10/103,832, filed on Mar. 25, 2002, now abandoned.

(30) Foreign Application Priority Data

Mar. 23, 2001 (JP) ............................... 2001-86309

(51) Int. Cl.
*G02B 5/28* (2006.01)

(52) U.S. Cl. ...................... 359/589; 210/650; 210/651; 252/586

(58) Field of Classification Search ................ 359/589, 359/580, 582, 584, 586; 534/573, 566; 436/164; 435/7.1; 422/1, 57, 68.1, 105, 108; 210/644, 210/650, 651, 739, 767; 252/586; 554/127
See application file for complete search history.

(56) References Cited

U.S. PATENT DOCUMENTS

| | | |
|---|---|---|
| 3,979,184 A | 9/1976 | Giaever |
| 3,985,617 A | 10/1976 | Yugari et al. |
| 4,350,761 A | 9/1982 | Yamamoto .................. 435/7.93 |
| 4,592,980 A | 6/1986 | Tomida et al. .............. 430/59.1 |
| 4,796,981 A | 1/1989 | Nishimura et al. ......... 359/289 |
| 4,810,639 A | 3/1989 | Pankratz ..................... 435/7.4 |
| 4,819,239 A | 4/1989 | Sharp et al. .................. 372/12 |
| 4,828,917 A | 5/1989 | Wegner et al. .............. 428/333 |
| 4,868,105 A | 9/1989 | Urdea ........................... 435/6 |
| 4,909,990 A | 3/1990 | Block et al. ............. 422/82.11 |
| 4,933,285 A | 6/1990 | Patton |
| 5,063,417 A | 11/1991 | Hopfield |
| 5,246,748 A | 9/1993 | Gillberg-Laforce et al. . 428/1.2 |
| 5,281,539 A | 1/1994 | Schramm ............... 204/403.11 |

(Continued)

FOREIGN PATENT DOCUMENTS

EP  1 288 662 A1  3/2003

(Continued)

OTHER PUBLICATIONS

Chudinova et al. "The study of the antigen-antibody reaction by fluorescence method in LB films for immunosensor", Thin Solid Films 307 (1997) 294-297.*

(Continued)

*Primary Examiner*—James Housel
*Assistant Examiner*—Christine Foster
(74) *Attorney, Agent, or Firm*—Sughrue Mion, PLLC

(57) ABSTRACT

A particle size (or particle diameter) variable reactor comprises a granular substrate and a capturing unit fixed onto the surface of the granular substrate. The capturing unit comprises a rod-shaped body having a length of 810 nm or less, a configuration variable element which may be structurally transformed when stimulation is applied, and a capturing structured body which specifically captures an object to be captured. The particle size variable reactor is highly biodegradable and environmentally friendly, and can specifically act on and thus selectively capture its target alone. The reactor may preferably be used in various fields including medical and industrial fields.

12 Claims, 9 Drawing Sheets

U.S. PATENT DOCUMENTS

| | | | |
|---|---|---|---|
| 5,304,631 | A | 4/1994 | Stewart et al. |
| 5,354,654 | A | 10/1994 | Ligler et al. ............... 435/5 |
| 5,756,296 | A | 5/1998 | Cubicciotti |
| 5,759,447 | A | 6/1998 | Efron et al. ............ 252/582 |
| 5,766,784 | A | 6/1998 | Baskaran et al. ......... 428/702 |
| 5,783,392 | A | 7/1998 | Seibl et al. ............... 435/6 |
| 5,800,994 | A | 9/1998 | Martinelli ............... 435/6 |
| 5,883,875 | A | 3/1999 | Coufal et al. |
| 6,083,689 | A | 7/2000 | Martinelli et al. .......... 435/6 |
| 6,087,100 | A | 7/2000 | Meade et al. |
| 6,096,273 | A | 8/2000 | Kayyem et al. |
| 6,124,963 | A | 9/2000 | Schumaker ............. 359/245 |
| 6,238,864 | B1 | 5/2001 | Yan ...................... 435/6 |
| 6,248,539 | B1 | 6/2001 | Ghadiri et al. |
| 6,306,584 | B1 | 10/2001 | Bamdad |
| 6,400,489 | B1 | 6/2002 | Suzuki et al. ............ 359/241 |
| 6,451,543 | B1 | 9/2002 | Kochendoerfer et al. .... 435/7.1 |
| 6,686,150 | B1 | 2/2004 | Blackburn et al. .......... 435/6 |
| 6,699,667 | B1 | 3/2004 | Keen |
| 6,839,175 | B1 | 1/2005 | Washizu |
| 2002/0139961 | A1 | 10/2002 | Kinoshita et al. |
| 2002/0168291 | A1 | 11/2002 | Kinoshita et al. |
| 2002/0168666 | A1 | 11/2002 | Kinoshita et al. |
| 2002/0168667 | A1 | 11/2002 | Kinoshita et al. |
| 2002/0168756 | A1 | 11/2002 | Kinoshita et al. |
| 2003/0003476 | A1 | 1/2003 | Kinoshita et al. |
| 2003/0179381 | A1 | 9/2003 | Kinoshita et al. |
| 2004/0136643 | A1 | 7/2004 | Washizu et al. |
| 2004/0156749 | A1 | 8/2004 | Washizu et al. |

FOREIGN PATENT DOCUMENTS

| | | |
|---|---|---|
| GB | 2 245 971 A1 | 1/1992 |
| JP | 63-222248 | 9/1988 |
| JP | 04-009743 | 1/1992 |
| JP | 07/075598 | 3/1995 |
| JP | 11-183479 | 7/1999 |
| JP | 2000-004054 A * | 1/2000 |
| JP | 2000-249644 | 9/2000 |
| WO | WO 96/26435 | 8/1996 |
| WO | WO 01/12665 A2 | 2/2001 |

OTHER PUBLICATIONS

Higuchi et al. "Photocontrol of Molecular Orientation of a Photoresponsive Amphiphilic alpha-Helix in a Lipid Monolayer", Langmuir 1997, 13, 1616-1622.*

Thomas M. Cooper, et. Al., "Formation of Polypeptide-Dye Multilayers by an Electrostatic Self-Assembly Technique," LANGMUIR 1995, vol. 11, No. 7, pp. 2713-2718.

Munekazu Date, et al., "52.3: Direct-viewing Display Using Alignment-controlled PDLC and Holographic PDLC," SID 00 Digest pp. 1184-1187.

Robert J. Collier, et al, "Optical Holography," Chapter 9, §§9.1 & 9.2, pp. 228-233. Academic Press, New York.

Baril et al, "Chromatography of ribonuclease treated myosin extracts from early embryonic chick muscle," Science (1964) 146:413-414.

Liu, et al., "Cell-ELISA using B-galactosidase conjugated antibodies" Journal of Immunological Methods 234 (Feb. 2000) p. 153-167).

Buchel, M. et al., "Langmui-Blodgett-Kuhn Multilayers of Polyglutamates with Azobenzene Moieties: Investigations of Photoinduced Changes in the Optical Properties and Structure of the Films," Langmuir 1995, vol. 11, p. 4460-4466.

Menzel, H. et al., "Small-Angle X-ray Scattering and Ultraviolet-Visible Spectroscopy Studies on the Structure and Structural Changes in Langmuir-Blodgett Films of Polyglutamates with Azobenzene Moieties Tethered by Alkyl Spacers of Different Lengths" Langmuir 1994, vol. 10, p. 1926-1933.

Okahata, Y. et al., "Orientation of DNA Double Strands in a Langmuir-Blodgett Film," Langmuir 1966, vol. 12, p. 1326-1330.

Parazak, D.P. et al., "Comparison of Host-Guest Langmuir-Blodgett Multilayer Formation by Two Different Amphiphilic Cyclodextrins," Langmuir 1996, vol. 12, p. 4046-4049.

Greenham et al, "Charge separation and transport in conjugated-polymer/semiconductor-nanocrystal composites studied by photoluminescence quenching and photoconductivity," Physical Review-B, 1996, 54(24), pp. 17628-17637.

S. Sugai et al., Poly($\gamma$-alkyl Glutamates), Journal of Polymer Science: Part A-2, vol. 4, 183-198 (1966).

Crick, F.H.C., The Packin g of $\alpha$-Helices: Simple Coiled-Coils, Acta Cryst (1953) 6, 689-697.

Minamoto, Y. et al., Polymethylglutamate as a New Matrix for Covalently Immobilized Enzymes: Preparation and Properties of Urease and Uricase, Biotech and Bioeng'n, vol. XXII, pp. 1225-1235 (1980).

Kinoshita, T., "Structural color forming system composed of polypeptide-based LB films," *Nanotechnology and Nano-Interface Controlled Electronic Devices*, Chapter 13, 2003, pp. 233-252.

Miyagi, T. "Structural Color with Polypeptide LB Film," *Transactions of the Materials Research Society of Japan*, 27 3, 555-558 (2002).

Yokoi, H., "Polypeptide membranes at an interface," Prog. Polym. Sci., pp. 341-357, 2003.

Color Tone Control By External Stimuli, Nagoya Institute of Technology, Imitating Function of Bio-skins Applicable to Display Devices, *Nikkan Kogyo Shinbun*, Dec. 28, 2000, Japan.

T. Doi et al., Symposium: Building of Molecular Composition and Its Function, Building and control of peptide type signal transfer function, A506, Nagoya Institute of Technology, Symposium held by JST, Nov. 28, 2000, Japan.

H. Yokoi et al., Preparation of Amphiphilic $\alpha$-helix LB film, *Polymer Preprints, Japan*, vol. 49 No. 12 IS07, Nagoya Institute of Technology, 2000, Society of Polymer Science, Japan.

H. Yokoi et al., Evaluation of molecular orientation of amphiphilic $\alpha$-helix water surface monomolecular film, *Polymer Preprints, Japan*, vol. 49 No. 13 Iipd090, Nagoya Institute of Technology, 2000, Society of Polymer Science, Japan.

Y. Okahata, Sensing of Odorous and Bitter Substances by using a Bilayer Molecular Film-coated Quartz Oscillator, *Biophysics*, vol. 28, No. 6 Pandect, Tokyo Institute of Technology, 1988, Japan.

Y. Okahata, Prospect for Chemical Information Conversion Membrane, Molecular Recognition to be realized on a Lipid Bilayer Molecular Membrane, *SEN-I Gakkaishi* (*Fiber and Industry*) vol. 46, No. 2 Feature: Functional Macromolecular Membranes Films, 1990, Japan.

K. Ariga et al., Evaluation of the Viscoelasticity of the Membrane with the Use of a Quartz Oscillator, Phase Transition of the LB film , vol. 28 No. 11, Tokyo Institute of Technology, 1990, Japan.

H. Yokoi et al., *The 48th Symposium on Macromolecules*, The Two Dimensional Orientation Control of Amphiphilic $\alpha$- helix Molecule. II P f094, Nagoya Institute of Technology, Oct. 6, 1999, Niigata, Japan.

H. Yokoi et al., *The 49th Annual Meeting of the Society of Polymer Science, Japan (SPSJ)*, The pH Dependence of Molecular Orientation in Monolayer Composed of Amphiphilic αhelix Molecule at Air-water Interface, I p. 173, Nagoya Institute of Technology, May 29, 2000, Nagoya, Japan.

H. Yokoi et al., *The 49th Symposium on Macromolecules*, Preparation of LB Film consisting of Amphiphilic α-helix Molecule, IS 07, Nagoya Institute of Technology, Sep. 27, 2000, Sendai, Japan.

H. Yokoi et al., *The 49th Symposium of Macromolecules*, Evaluation of molecular orientation of amphiphilic α-helix water surface monomolecular film, IIPd090, Nagoya Institute of Technology, Sep. 27, 2000, Sendai, Japan.

Y. Nagata, et al., *The 43rd Annual Meeting of the Society of Polymer Science, Japan (SPSJ)*, Preparation and Function of Polypeptide Containing a Substrate-binding Site at the Molecular Terminal, II-9-06, Nagoya Institute of Technology, and National Institute of Materials and Chemical Research, Tsukuba, May 26, 1994, Nagoya, Japan.

H. Hosokawa et al., *The 44th Annual Meeting of the Society of Polymer Science, Japan (SPSJ)*, Functional Control of Polypeptide Containing an Inclusion Terminal Group, II Pel 119, May 30, 1995, Yokohama, Japan.

H. Hosokawa et al., Functional Control of Polypeptide Containing an Inclusion Terminal Group, Preprints of Annual meeting of the Society of Fiber Science and Technology, Japan, G-264 3G17, Jun. 29, 1995, Tokyo (Sen-I Gakkai).

H. Hosokawa et al., *45th Annual Meeting of Society of Polymer Science of Japan*, Monolayer of polypeptide containing a cyclodextrin at the terminal, IIIPb100, Nagoya Institute Technology, Nagoya and National Institute of Materials and Chemical Research, Tsukuba, May 29, 1996, Nagoya, Japan.

H. Hosokawa et al., *45th Symposium of Society of Polymer Science of Japan*, Molecular Orientation of polypeptide containing a cyclodextrin at the terminal in the monolayer and its function, 2Pb44, Nagoya Institute of Technology, Oct. 2, 1996, Hiroshima, Japan.

H. Hosokawa et al., *46th Annual Meeting of Society of Polymer Science of Japan*, Structural control of polypeptide containing an active site at the terminal in monolayer and its function, IIPb108, Nagoya Institute of Technology, May 24, 1997, Tokyo, Japan.

A. Kato et al., *47th Annual Meeting of Society of Polymer Science of Japan*, Characterization of polypeptide monolayer containing the molecular recognition site, IIIPd124, Nagoya Institute of Technology, May 29, 1998, Kyoto, Japan.

A. Kato et al., *29th Annual Meeting of Union of Chemistry-Related Societies in Chubu Area, Japan*, Characterization of polypeptide monolayer containing a cyclodextin at the terminal, 1B0705, Nagoya Institute of Technology, Oct. 3, 1998, Toyohashi, Japan.

H. Yokoi et al., The control of molecular orientation in monolayer of amphiphilic α-helix, *Preprints presented at 15th Symposium of Membrane Science and Technology*, 3PA53, Nagoya Institute of Technology and Core Research for Evolutional Science and Technology, May 12, 1999, Chiba, Japan (Sen-I Gakkai).

T. Doi et al., *48th Symposium of Society of Polymer Science of Japan*, The molecular orientation and oscillation of polypeptide monolayer at oil/water interface, 111J02, Nagoya Institute of Technology and Core Research for Evolutional Science and Technology, Oct. 8, 1999, Niigata, Japan.

T. Doi et al., *Open Symposium of Creation and Functions of New Molecules and Molecular Assemblies sponsored by Core Research for Evolutional Science and Technology (CREST)*, Creation of peptide-type signal transmitting function and control of its function, A506, Nagoya Institute of Technology, Nov. 28, 2000, at Japan Science and Technology Corporation (JST), Tokyo, Japan.

T. Doi, Molecular alignment of poly(γ-methyl-L-glutamate) containing a β-cyclodextrin at the terminal and molecular identification (n-hexane/water interface), *Control of molecular alignment of polypeptide molecular film* published by Dr. Tomokiyo Doi, chapter 4, 2000.

Kinoshita et al, Preparation of a structural color forming system by polypeptide-based Ib films. The fourth NIMC International Symposium on Photoreaction Control and Photofunctional Materials. Mar. 14, 2001, pp. 1-9-1-12.

Yokoi et al, "Nano-phase Separation in the Monolayer Composed of α-Helical Copolypeptide at Air/Water Interface." Chemistry Letters 2000. Jul. 13, 2000, pp. 1210-1211. The chemical Society of Japan.

Mouri et al "The molecular recognition and polypeptide orientation in the monolayer at oil/water interface." 12th Academic Symposium of MRS Japan manuscripts. Dec. 7, 2000, p. 66.

Hosokawa et al, "The molecular orientation of a peptide-based amphiphile at hexane/water interface." Chemistry Letters 1997. Apr. 9, 1997, pp. 745-746. The Chemical Society of Japan.

Kinoshita et al, "The guest-induced oscillation of a monolayer composed of polypeptide containing β-cyclodextrin at the terminal." Chaos, vol. 9, No. 2, Jan. 19, 1999, pp. 276-282.

Doi, et al "The Control of Structure and Functions of LB-Film Composed of Bio-Related Polymers," 1st Int'l Symposium on Biomimetic Materials Processing, Jan. 11, 2001, in Nagoya, p. 19.

Kinoshita, T., "Control of Superfine Structure of Membrance and Their Characterization," *Polymer*, vol. 50, Dept. of Eng'g, Nagoya Institute of Technology, pp. 648-651, Sep. 2001.

Kawaguchi, T., "A Device For Visual Detection of Antigens and Antibodies By Means of Light Interference," *Thin Solid Films*, vol. 191, pp. 369-381, 1990.

* cited by examiner

PARTICLE SIZE VARIABLE REACTOR

This application is a divisional of application Ser. No. 10/103,832, filed Mar. 25, 2002, now abandoned.

BACKGROUND OF THE INVENTION

1. Field of the Invention

The present invention relates to a highly biodegradable and less harmful, particle size (or particle diameter) variable reactor that can specifically capture a target and has a particle size, flow rate, capturing reaction rate and ability to pass through a filter membrane which are adjustable. The inventive particle size variable reactor can be used in various fields.

2. Description of the Related Art

Devices which can specifically act on and thus selectively capture a particular target alone have been developed and utilized in various fields including medical and industrial fields.

Today, however, because of recent increasing public interest in environmental pollution, a nature-friendly device is now demanded which can selectively capture a particular target in an aqueous and/or oil phase and produce highly biodegradable and less harmful waste materials including the object captured.

SUMMARY OF THE INVENTION

In order to solve the above-described problems associated with the prior art, an object of the present invention is to provide a highly biodegradable and less harmful particle size (or particle diameter) variable reactor that can specifically act on and selectively capture an object to be captured, which can be preferably used in various fields including medical and industrial fields.

DESCRIPTION OF THE PREFERRED EMBODIMENTS

Figure 1:
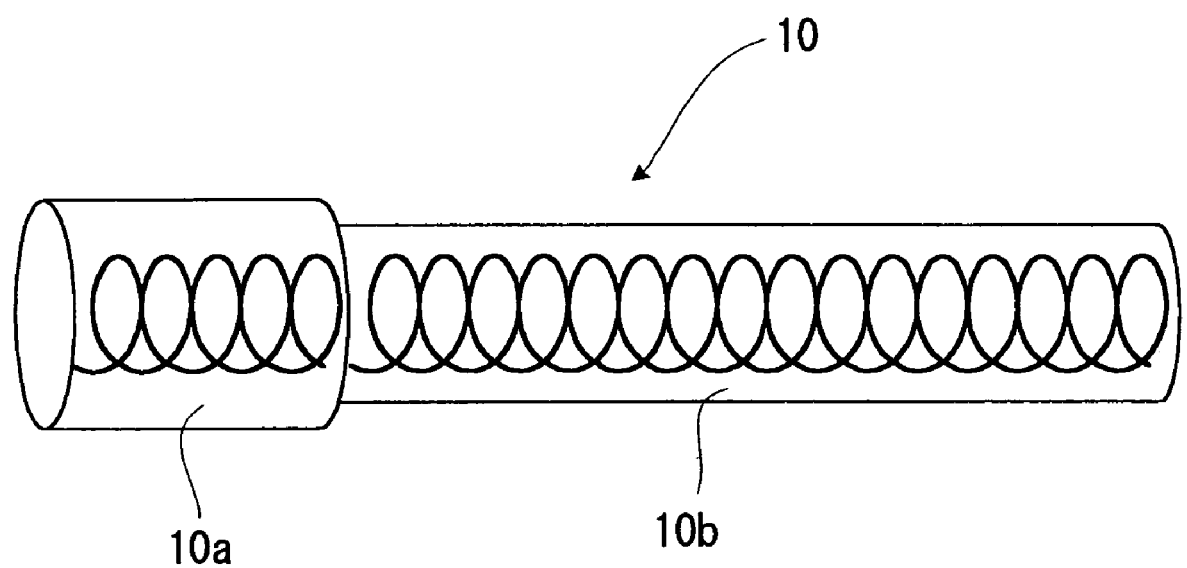
FIG. 1 is a schematic view showing one embodiment of the amphiphilic rod-shaped body according to the present invention.

The particle size (or particle diameter) variable reactor according to the present invention comprises a granular substrate and a capturing unit fixed onto the surface of the granular substrate.

{Capturing Unit}

The capturing unit comprises a rod-shaped body, a configuration variable element and a capturing structured body.

<Rod-Shaped Body>

The above-described rod-shaped body may be any rod-shaped material which can suitably be selected depending on a particular purpose, including inorganic and organic rod-shaped bodies, and preferably organic rod-shaped bodies.

Organic rod-shaped bodies include biopolymers and polysaccharides.

Examples of biopolymers preferably include fibrous proteins, α-helix polypeptides and nucleic acids (DNA, RNA, etc.). Fibrous proteins include those having an α-helix structure such as α-keratin, myosin, epidermin, fibrinogen, tropomyosin, silk fibroin or the like. A preferable example of polysaccharide is amylose.

Preferable examples of organic rod-shaped bodies are those having a helix structure in the molecule since they can stably keep their rod-shaped structures and intercalate other substance or substances of interest therein when desirable, including α-helix polypeptides, DNAs and amylose among those described above.

{α-Helix Polypeptide}

The above-described α-helix polypeptides are polypeptides having a certain type of secondary structure in which every 3.6 amino acids form one coil and an imide group (—NH—) and a carbonyl group (—CO—) at every fourth amino acid in each of the two strands in the helix are bridged by a hydrogen bond which extends substantially parallel to the helix core. In this α-helix structure, repeat subunits each consisting of 7 amino acids are linked one another to form an energy-stable structure.

The above-described α-helix polypeptide may be either dextral or sinistral. It should be noted that all of the naturally-occurring α-helix polypeptides are dextral due to its stability.

Any amino acids which are capable of forming an α-helix structure may be used to form the above-described α-helix polypeptide and can be suitably selected depending on a particular purpose. Preferably, amino acids which are likely to form an α-helix structure may be used, including, for example, aspartic acid (Asp), glutamic acid (Glu), arginine (Arg), lysine (Lys), histidine (His), asparagine (Asn), glutamine (Gln), serine (Ser), threonine (Thr), alanine (Ala), valine (Val), leucine (Leu), isoleucine (Ile), cysteine (Cys), methionine (Met), tyrosine (Tyr), phenylalanine (Phe) and tryptophan (Trp). Amino acids may be used alone or in combination.

The above-described α-helix polypeptide may be either hydrophilic, hydrophobic or amphiphilic depending on the amino acids selected. For hydrophilic α-helix polypeptides, serine (Ser), threonine (Thr), aspartic acid (Asp), glutamic acid (Glu), arginine (Arg), lysine (Lys), asparagine (Asn) and glutamine (Gln) may be preferably used. For hydrophobic α-helix polypeptides, phenylalanine (Phe), tryptophan (Trp), isoleucine (Ile), tyrosine (Tyr), methionine (Met), leucine (Leu) and valine (Val) may be used.

In the above-described α-helix polypeptides, carboxyl groups in those amino acids forming the α-helix which do not contribute to peptide bonds can be esterified to obtain hydrophobic polypeptides while the esterified carboxyl groups can be hydrolyzed to obtain hydrophilic polypeptides.

Amino acids may either be L-amino acids, D-amino acids, or derivatives thereof with modified side chains.

The number of bonds (the degree of polymerization) of the amino acid in the α-helix polypeptide is not particularly limited and may be appropriately selected in accordance with the object. However, 10 to 5000 is preferable.

If the number of bonds (the degree of polymerization) is less than 10, it may not be possible for the polyamino acid to form a stable α-helix. If the number of bonds (the degree of polymerization) exceeds 5000, vertical orientation may be difficult to achieve.

Suitable specific examples of the α-helix polypeptide are polyglutamic acid derivatives such as poly(γ-methyl L-glutamate), poly(γ-ethyl L-glutamate), poly(γ-benzyl L-glutamate), poly(n-hexyl L-glutamate), and the like; polyaspartic acid derivatives such as poly(β-benzyl L-aspartate) and the like; polypeptides such as poly(L-leucine), poly(L-alanine), poly(L-methionine), poly(L-phenylalanine), poly(L-lysine)-poly(γ-methyl L-glutamate), and the like.

The α-helix polypeptide may be a commercially available α-helix polypeptide, or may be appropriately synthesized or prepared in accordance with methods disclosed in known publications and the like.

As one example of synthesizing the α-helix polypeptide, the synthesis of block copolypeptide [poly(L-lysine)$_{25}$-poly(γ-methyl L-glutamate)$_{60}$]PLLZ$_{25}$-PMLG$_{60}$ is as follows. As is shown by the following formula, block copolypeptide [poly(L-lysine)$_{25}$-poly(γ-methyl L-glutamate)$_{60}$]PLLZ$_{25}$-PMLG$_{60}$ can be synthesized by polymerizing N$^\epsilon$-carbobenzoxy L-lysine N$^\alpha$-carboxy acid anhydride (LLZ-NCA) by using n-hexylamine as an initiator, and then polymerizing γ-methyl L-glutamate N-carboxy acid anhydride (MLG-NCA).

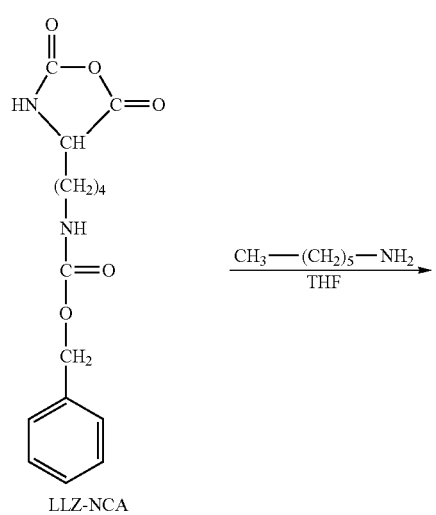

LLZ-NCA

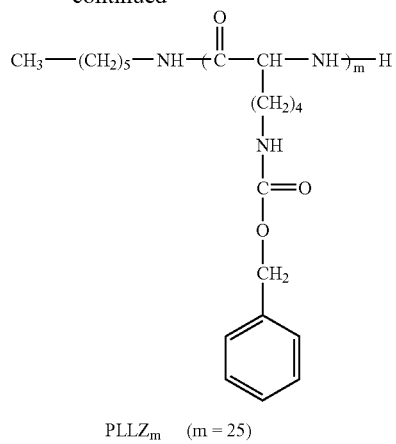

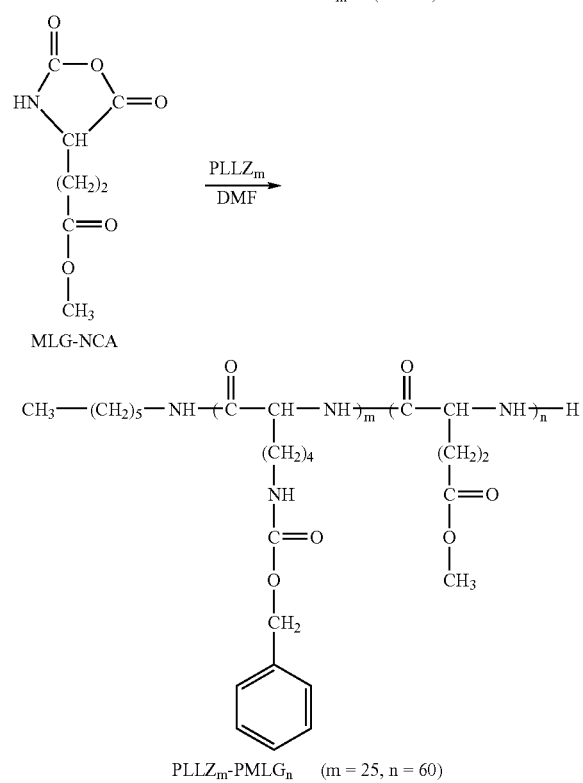

Synthesis of the α-helix polypeptide is not limited to the above-described method, and the α-helix polypeptide can be synthesized by a genetic engineering method. Specifically, the α-helix polypeptide can be manufactured by transforming a host cell by a expression vector in which is integrated a DNA which encodes the object polypeptide, and culturing the transformant, and the like.

Examples of the expression vector include a plasmid vector, a phage vector, a plasmid and phage chimeric vector, and the like.

Examples of the host cell include prokaryotic microorganisms such as *E. coli, Bacillus subtilis,* and the like; eukaryotic microorganisms such as yeast or the like; zooblasts, and the like.

The α-helix polynucleotide may be prepared by removing the α-helix structural portion from a natural fibrous protein such as α-keratin, myosin, epidermin, fibrinogen, tropomyosin, silk fibroin, or the like.

{DNA}

The DNA may be a single-stranded DNA. However, the DNA is preferably a double-stranded DNA from the standpoints that the rod-shape can be stably maintained, other substances can be intercalated into the interior, and the like.

A double-stranded DNA has a double helix structure in which two polynucleotide chains, which are in the form of right-wound spirals, are formed so as to be positioned around a single central axis in a state in which they extend in respectively opposite directions.

The polynucleotide chains are formed by four types of nucleic acid bases which are adenine (A), thiamine (T), guanine (G), and cytosine (C). The nucleic acid bases in the polynucleotide chain exist in the form of projecting inwardly within a plane which is orthogonal to the central axis, and form so-called Watson-Crick base pairs. Thiamine specifically hydrogen bonds with adenine, and cytosine specifically hydrogen bonds with guanine. As a result, in a double-stranded DNA, the two polypeptide chains are bonded complementarily.

The DNA can be prepared by known methods such as PCR (Polymerase Chain Reaction), LCR (Ligase Chain Reaction), 3SR (Self-Sustained Sequence Replication), SDA (Strand Displacement Amplification), and the like. Among these, the PCR method is preferable.

Further, the DNA can be prepared by being directly removed enzymatically from a natural gene by a restriction enzyme. Or, the DNA can be prepared by a genetic cloning method, or by a chemical synthesis method.

In the case of a genetic cloning method, a large amount of the DNA can be prepared by, for example, integrating a structure, in which a normal nucleic acid has been amplified, into a vector which is selected from plasmid vectors, phage vectors, plasmid and phage chimeric vectors, and the like, and then introducing the vector into an arbitrary host in which propagation is possible and which is selected from prokaryotic microorganisms such as *E. coli, Bacillus subtilis*, or the like; eukaryotic microorganisms such as yeast or the like; zooblasts, and the like.

Examples of chemical synthesis methods include liquid phase methods or solid phase synthesis methods using an insoluble carrier, such as a tolyester method, a phosphorous acid method, or the like. In the case of a chemical synthesis method, the double-stranded DNA can be prepared by using a known automatic synthesizing device or the like to prepare a large amount of single-stranded DNA, and thereafter, carrying out annealing.

{Amylose}

Amylose is a polysaccharide having a spiral structure in which D-glucose, which forms starch which is a homopolysaccharide of higher plants for storage, is joined in a straight chain by $\alpha$-1,4 bonds.

The molecular weight of the amylose is preferably around several thousand to 150,000 in number average molecular weight.

The amylose may be a commercially available amylose, or may be appropriately prepared in accordance with known methods.

Amylopectin may be contained in a portion of the amylose.

The length of the rod-shaped body is not particularly limited, and may be appropriately selected in accordance with the object. However, from the standpoint of causing light reflection of an incident light as colored interference light, which will be described later, a length of 810 nm or less is preferable, and 10 nm to 810 nm is more preferable.

The length of diameter of the rod-shaped body is not particularly limited, and in the case of $\alpha$-helix polypeptides, it is approximately 0.8 to 2.0 nm.

The entire rod-shaped body may be hydrophobic or hydrophilic. Or, the rod-shaped body may be amphiphilic such that a portion thereof is hydrophobic or hydrophilic, and the other portion thereof exhibits the opposite property of the one portion. When the rod-shaped body is amphiphilic, it is advantageous in that orientation or dispersion at the boundary face in oil-phase-aqueous phase mixtures, and gaseous phase-liquid phase mixtures becomes easy.

In the case of an amphiphilic rod-shaped body, the numbers of the lipophilic (hydrophobic) portions and hydrophilic portions are not particularly limited, and may be appropriately selected in accordance with the object. Further, in this case, the portions which are lipophilic (hydrophobic) and the portions which are hydrophilic may be positioned alternately, or either type of portion may be positioned only at one end portion of the rod-shaped body.

In the case of the amphiphilic rod-shaped body, there is no particular limitation for the numbers of the moiety showing hydrophobicity and the moiety showing hydrophilicity but that may be appropriately selected according to the object. In that case, the moiety showing hydrophobicity and the moiety showing hydrophilicity may be alternately positioned. Any of the moieties may be positioned only at one end of the rod-shaped body.

One example of the above-described amphiphilic rod-shaped structure is shown in FIG. 1. In this Figure, a rod-structured element 10 comprises a hydrophobic part 10a at one end and a hydrophilic part 10b at the other end thereof.

{Configuration Variable Element}

Any material which can be structurally transformed by stimulation may be used as the configuration variable element and the material can be selected depending on a particular purpose.

Stimulation includes chemical stimulation and physical stimulation.

Examples of chemical stimulation include pH change and co-existence of a certain substance. Examples of physical stimulation include those using light, electric field, heat, magnetic field and pressure, and preferably light, electric field and heat.

Examples of configuration variable element that can be structurally transformed when exposed to light include photo chemically reactive compounds, including photoreactive ring-opening compounds such as spirobenzopyran, compounds having photo ionization functional groups and stereoisomers.

Geometrical stereoisomers may preferably be used as stereoisomers since they can be structurally transformed to develop color when exposed to light.

Those materials that can be structurally transformed when exposed to light may be used alone or in combination.

Those materials that can be structurally transformed when an electric field is applied include, for example, liquid crystalline molecules.

Examples of liquid crystalline molecules include rod-shaped liquid crystalline molecules and discotic liquid crystalline molecules.

Examples of rod-shaped liquid crystalline molecules include azomethine compounds, azoxy compounds, cyan biphenyl compounds, cyanophenylester compounds, ester benzoate compounds, cyclohexane carboxylic phenylester compounds, cyanophyenylcyclohexane compounds, cyano-substitution phenylpyrimidine compounds, alkoxy-substituted phenylpyrimidine compounds, phenyldioxane compounds, tolan compounds and alkenylcyclohexyl benzonitrile compounds. Preferably, rod-shaped liquid crystalline molecules may also include liquid crystal polymer molecules.

Discotic liquid crystalline molecules include compounds disclosed in literatures such as C. Destrade, et al., Mol. Crysr. Liq. Cryst., vol. 71, p. 111 (1981); Japan Chemical Association eds., Kikan Kagaku Sosetsu, No. 22, Chemistry of Liquid Crystal, Chapter 5, and Chapter 10, Section 2. (1994); B. Kohne et al., Angew, Chem. Soc. Chem. Comm. p. 1794 (1985); J. Zhang et al., J. Am. Chem. Soc., Vol. 116, p. 2655 (1994) and Japanese Patent Application Laid-Open Nos. 5-5837, 8-27284, 8-334621 and 9-104656.

Those materials that can be structurally transformed when an electric field is applied thereto may be used alone or in combination.

Those materials that can be structurally transformed when exposed to heat may include: those which exhibit thermal expansion or shrinkage; crystalline materials which will melt or materials which will be crystallized when heated; thermoplastic materials; thermosetting materials; and the above-described liquid crystalline molecules.

The above-described thermoplastic materials include thermoplastic resins, for example, and particularly polyethylene, polypropylene, polyvinyl chloride, polystyrene, polyvinylidene chloride, fluororesin or polymethyl methacrylate, condensation polymers of polyamide, polyester, polycarbonate, polyphenylene oxide, addition polymers of thermoplastic polyurethane, and ring-opening polymers of polyacetal.

The above-described thermosetting materials include thermosetting resins, and particularly urea resin, melamine resin and phenolic resin.

Those materials that can be structurally transformed when exposed to heat may be used alone or in combination.

Preferably, these configuration variable elements can be reversibly transformed so that they can be suitably used in various situations where the control of color to be developed is required. For this purpose, geometrical isomers and liquid crystalline molecules are preferable, and geometrical isomers are more preferable.

Any geometrical isomers that can be structurally transformed when exposed to light may be used, including cis-trans isomers and syn-anti isomers. Particularly, compounds having an azo group (—N=N—) such as azo compounds and azoxy compounds are preferable.

Examples of azo compounds include azobenzene compounds, azomethane compounds, azodicarbonamide compounds and diethyl azodicarboxylate compounds.

Examples of azoxy compounds include azoxydibenzate compounds and azoxybenzene compounds.

Structural change in the above-described azobenzene compound caused by irradiation with light will be described below. An azobenzene compound (trans-isomer) may typically have an absorption band of 300–400 nm and the distance between the distal ends of the two benzene rings (of which the distal ends being located at the para-positions with respect to the azogroup by which the two benzene rings are bridged) is about 9.0 Å (see (a) below). Irradiation of the azobenzene compound with UV light may cause the transformation of the azobenzene compound from trans- to cis-isomer in which the distance between the distal ends of its benzene rings is about 5.5 Å (see (b) below), resulting in preferable color change.

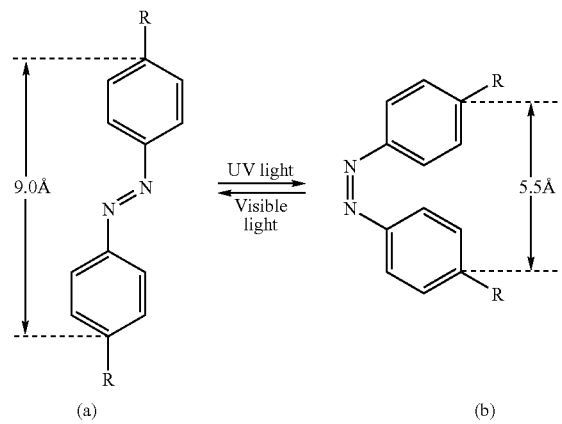

Formula 2

Figure 2:
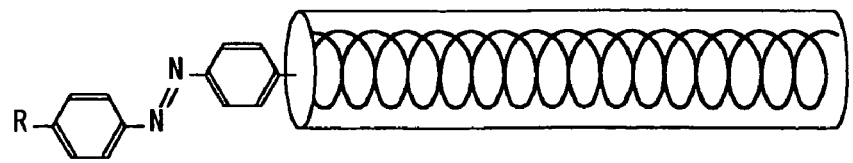
FIG. 2 is a schematic view showing one embodiment of a rod-shaped body according to the present invention which has a configuration variable element attached to one end of the linear chain thereof.
Figure 3:
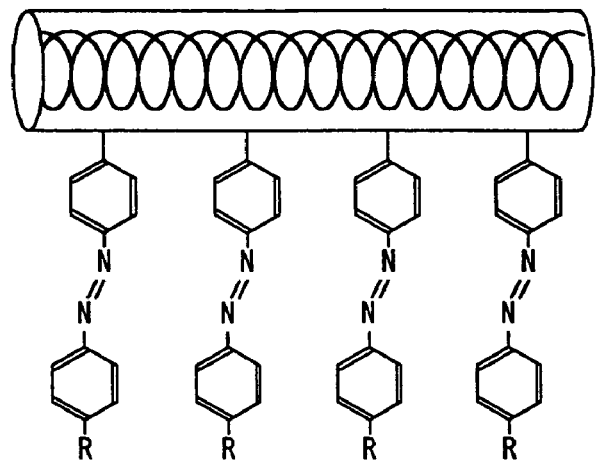
FIG. 3 is a schematic view showing another embodiment of the rod-shaped body according to the present invention which has configuration variable elements attached to the side chains thereof.
Figure 4:
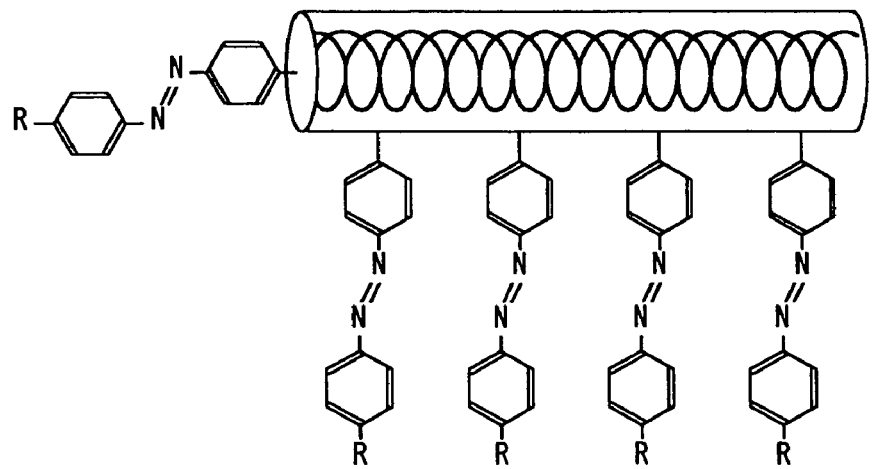
FIG. 4 is a schematic view showing another embodiment of the rod-shaped body according to the present invention which has configuration variable elements attached to both one end of the linear chain and the side chains thereof.

A configuration variable element or components may be bonded to one end of the linear chain (as shown in FIG. 2), to the side chain or chains (as shown in FIG. 3), or both to one end of the linear chain and to the side chain(s) (as shown in FIG. 4) of the above-described rod-shaped body. Preferably, a configuration variable element may be bonded at least to one end of the linear chain of a rod-shaped body for better color change.

When a configuration variable element or components are bonded to the side chain or chains of the above-described rod-shaped body, any percentage of the total side chains of the rod-shaped body may be bonded by configuration variable element(s) and can be desirably selected.

<Capturing Structured Body>

Capturing structured bodies include any structures which can capture or trap a particular target of interest, and can be suitably selected depending on a particular purpose.

Examples of capturing modes include, but are not limited to, physical adsorption and chemical adsorption. A capturing (coupling) structure may be formed, for example, via a hydrogen bond, intermolecular forces (Van der Waals forces), coordinate bonds, ionic bonds, or covalent bonds.

Particular examples of the above-described capturing structured body preferably include host components contained in clathrate compounds (hereinafter interchangeably referred to as a "host"), antibodies, nucleic acids, hormone receptors, lectin and physiologically active agent receptors. Among all, host components (contained in clathrate compounds) and antibodies are preferable.

A capturing structured body may capture its target; a host may capture its guest (a component to be included or captured) in an clathrate compound; an antibody may capture an antigen; a nucleic acid may capture another nucleic acid, tubulin, chitin or the like; a hormone receptor may capture a hormone; lectin may capture sugar or the like; and a physiologically active agent receptor may capture a physiologically active agent.

{Host in Clathrate Compound}

Any host contained in clathrate compound that has a molecular recognition ability (host-guest binding ability) may be used and can be selected depending on a particular purpose. Such hosts preferably include, for example, those having a tubular (one-dimensional), layer (two-dimensional) or cage-like (three-dimensional) cavity or cavities, and others.

Examples of the clathrate compounds having a tubular (one-dimensional) cavity include urea, thiourea, deoxycholic acid, dinitrodiphenyl, dioxytriphenylmethane, triphenylmethane, methylnaphthalene, spirochroman, PHTP (perhydrotriphenylene) cellulose, amylose and cyclodextrin. It should be noted that cyclodextrin may have a cage-like cavity in a solution.

Examples of the object (i.e., a guest) to be captured by urea include n-paraffin derivatives.

Examples of the object (e.g., a guest) to be captured by thiourea include branched or cyclic hydrocarbons.

Examples of the object (e.g., a guest) to be captured by deoxycholic acid include paraffins, fatty acids and aromatic compounds.

Examples of the object (e.g., a guest) to be captured by dinitrodiphenyl include diphenyl derivatives.

Examples of the object (e.g., a guest) to be captured by dioxytriphenylmethane include paraffins, n-alkenes and squalenes.

Examples of the object (e.g., a guest) to be captured by triphenylmethane include paraffins.

Examples of the object (e.g., a guest) to be captured by methylnaphthalene include $C_{1-16}$ n-paraffins and branched paraffins.

Examples of the object (e.g., a guest) to be captured by spirochroman include paraffins.

Examples of the object (e.g., a guest) to be captured by PHTP (perhydrotriphenylene) include chloroform, benzene and various polymers.

Examples of the object (e.g., a guest) to be captured by cellulose include $H_2O$, paraffins, $CCl_4$, colorants and iodine.

Examples of the object (e.g., a guest) to be captured by amylose include fatty acids and iodine.

Cyclodextrin is a cyclic dextrin produced by amylase digestion of starch. Three types of cyclodextrin are presently known, including α-cyclodextrin, β-cyclodextrin and γ-cyclodextrin. Cyclodextrin derivatives can also be used in the present invention, including those partially having OH-group(s) substituted by other functional group(s) such as alkyl, allyl, alkoxy, amide and/or sulfonic acid group(s).

Examples of the object (e.g., a guest) to be captured by cyclodextrin include: phenol derivatives such as thymol, eugenol, resorcin, ethylene glycol monophenylether or 2-hydroxy-4-methoxy-benzophenone; benzoate derivatives such as salicylic acid, methyl parahydroxybenzoate or ethyl parahydroxybenzoate and esters thereof; steroids such as cholesterol; vitamins such as ascorbic acid, retinol or tocopherol; hydrocarbons such as limonene; allyl isothiocyanate; sorbic acid; iodine molecule; Methyl Orange; Congo Red; and potassium 2-p-toluidinylnaphthalene-6-sulfonate (TNS).

Examples of layer (two-dimensional) hosts contained in clathrate compounds include clay minerals, graphite, smectites, montmorillonite and zeolite.

Examples of the object (i.e., a guest) to be captured by clay minerals include hydrophilic materials and polar compounds.

Examples of the object (i.e., a guest) to be captured by graphite include O, $HSO_4^-$, halogen, halides and alkali metals.

Examples of the object (i.e., a guest) to be captured by montmorillonite include brucine, codeine, o-phenylenediamine, benzidine, piperidine, adenine, guianine and liposide thereof.

Examples of the object (i.e., a guest) to be captured by zeolite include $H_2O$.

Examples of cage-like (three dimensional) host contained in clathrate compounds include hydroquinone, gaseous hydrates, tri-o-thymotide, oxyflavan, dicyanoammine nickel, cryptand, calixarene, and crown compounds.

Examples of the object (i.e., a guest) to be captured by hydroquinone include HCl, $SO_2$, acetylene and rare gas elements.

Examples of the object (i.e., a guest) to be captured by gaseous hydrate include halogen, rare gas elements and lower hydrocarbons.

Examples of the object (i.e., a guest) to be captured by tri-o-thymotide include cyclohexane, benzene and chloroform.

Examples of the object (i.e., a guest) to be captured by oxyflavan include organic bases.

Examples of the object (i.e., a guest) to be captured by dicyanoamminenickel include benzene and phenol.

Examples of the object (i.e., a guest) to be captured by cryptand include $NH^{4+}$ and various metal ions.

The Calixarene is a cyclic oligomer comprising phenol units polymerized via methylene groups which can be synthesized from phenol and formaldehyde under appropriate conditions. Calix[4–8]arenes are known. Examples of the object (i.e., a guest) to be captured by p-tert-butylcarixarene (n=4) may include, chloroform, benzene, toluene, and the like. Examples of an object to be captured (the guest) by the p-tert-butylcarixarene (n=5) may include, isopropyl alcohol, acetone, and the like. Examples of an object to be captured (the guest) by the p-tert-butylcarixarene (n=6) may include, chloroform, methanol, and the like. Finally, examples of an object to be captured (the guest) by the p-tert-butylcarixarene (n=7) may include, chloroform.

The crown compounds include a macrocyclic compound having not only a crown ether having oxygen as an electron-donating donor atom but also a donor atom such as nitrogen, sulfur, and the like as an analog thereof as constituting elements for a ring structure, and also includes a multicyclic crown compound comprising two or more rings represented by cryptand for example, and there may be exemplified cyclohexyl-12-crown-4, dibenzo-14-crown-4, tert-butyl-benzo-15-crown-5, dibenzo-18-crown-6, dicyclohexyl-18-crown-6,18-crown-6, tribenzo-18-crown-6, tetrabenzo-24-crown-8, dibenzo-26-crown-6, and the like.

Examples of the object (i.e., a guest) to be captured by a crown compound are: various metal ions including those of alkali metals such as Li, Na or K and alkali-earth metals such as Mg or Ca; $NH^{4+}$; alkyl ammonium ion; guanidium ion; and aromatic diazonium ion. Crown compounds may form complexes with those targets. Examples of the object (i.e., a guest) to be captured by a crown compound further include polar organic compounds which have a group of relatively stronger acidity such as C—H (e.g., acetonitrile, malonitrile and adiponitrile), N—H (e.g., aniline, aminobenzoic acid, amide and sulfamide derivatives) and/or O—H (e.g., phenol and acetate derivatives) unit or units. Crown compounds may also form complexes with these targets.

A host in an clathrate compound may have a cavity of any size which can be selected depending on a particular purpose. Hosts having a size of 0.1 nm–2.0 nm may be preferable since they can exhibit stable molecule recognition ability (host-guest binding ability).

The mixture ratio (molar ratio) of host to guest contained in an clathrate compound may depend on the type of the host and guest to be used. Typically, the host: guest ratio may be 1:0.1–1:10, and preferably 1:0.3–1:3.

{Antibody}

Any antibody which can specifically bind to its target antigen (the object to be captured) may be used, including polyclonal and monoclonal antibodies. Fab', Fab and F(ab')$_2$ fragments of IgG, IgM, IgE and IgG can also be used.

Any antigen may be used as the above-described target antigen and can be suitably selected depending on a particular purpose, including plasma proteins, tumor markers, apoproteins, viruses, auto antibodies, coagulation/fibrinolysis factor, hormones, blood drugs, and HLA antigens.

Figure 5:
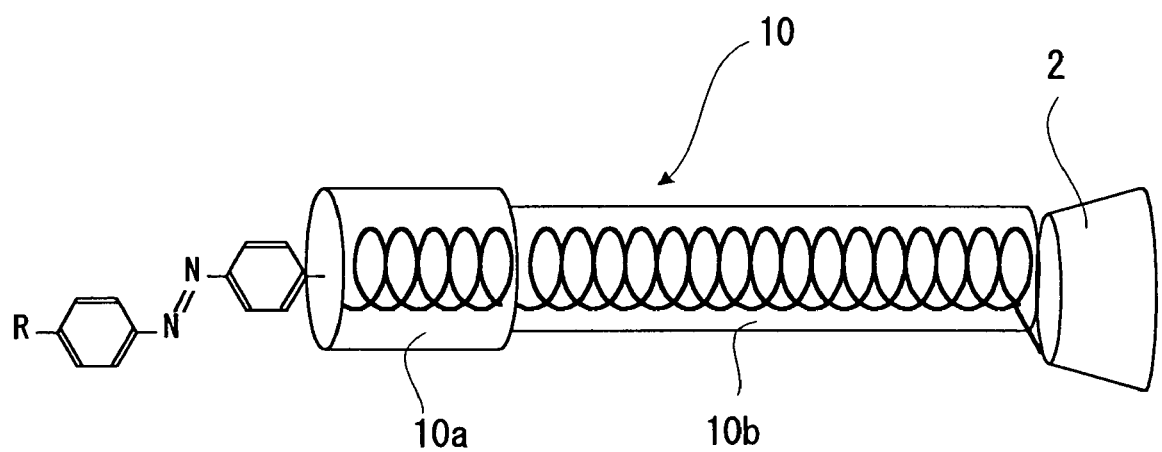
FIG. 5 is a schematic view showing another embodiment of an amphiphilic rod-shaped body according to the present invention which has a capturing structured body attached to one end and a configuration variable element attached to the other end of the rod-shaped body.

An exemplary amphiphilic rod-shaped body which has a capturing structured body and a configuration variable element bonded thereto is shown in FIG. 5. In this Figure, a rod-shaped body 10 comprises a hydrophobic part 10a at one end and a hydrophilic part 10b at the other end thereof, and has a capturing structured body 2 attached to one end and a configuration variable element (azobenzene compound) attached to the other end of the rod-shaped body 10. A plurality of capturing structured bodies 2 may be bonded to the side surface of the rod-shaped body 10.

<Reflection of the Incident Light as Colored Interference Light>

Preferably, the above-described capturing unit can exhibit color forming so that it can easily be detected and identified.

Color forming may include color formation using colorant (e.g., dyes and/or pigments), which is based on a chemical structure, in which electron transition may occur when exposed to light thereby developing color, as well as by reflecting an incident light as colored interference light (e.g., those found in tropical fish or phosphorus powder on butterfly wing), which is based on a physical structure, in which a color tone may change corresponding to the thickness of the membrane (layer) and its refractive index.

Reflection of the incident light as colored interference light is based on the multi-layered thin film interference principle, the basic principle of color forming exhibited by the scaly powder of the wings of a Morpho butterfly and, when an external stimulation such as an electric field, a magnetic field, heat or light (e.g., natural light, infrared ray or UV light) is applied to a material which exhibits light reflection of the incident light as colored interference light (e.g., membrane or layer), a portion of the incident light which has a wavelength of a particular range will be reflected corresponding to the thickness of the material which exhibits light reflection of the incident light as colored interference light (membrane or layer) to be used as well as to its refractive index, whereby the surface of the material which exhibits light reflection of the incident light as colored interference light may exhibit color. Its color tone may be suitably regulated (as found on the skin of the chameleon) depending on the external stimulation to be applied.

Among all, a light reflection of the incident light as colored interference light may be preferable for the present invention since it may not require use of dyes or pigments and can thus reduce the volume of liquid waste resulting from manufacturing processes and can economize on energy (water and electricity) required for dying processes as well as it is human/nature-friendly without causing dye- or pigment-induced skin trouble and so on.

The principle of light reflection of the incident light as colored interference light will be described below.

Figure 6:
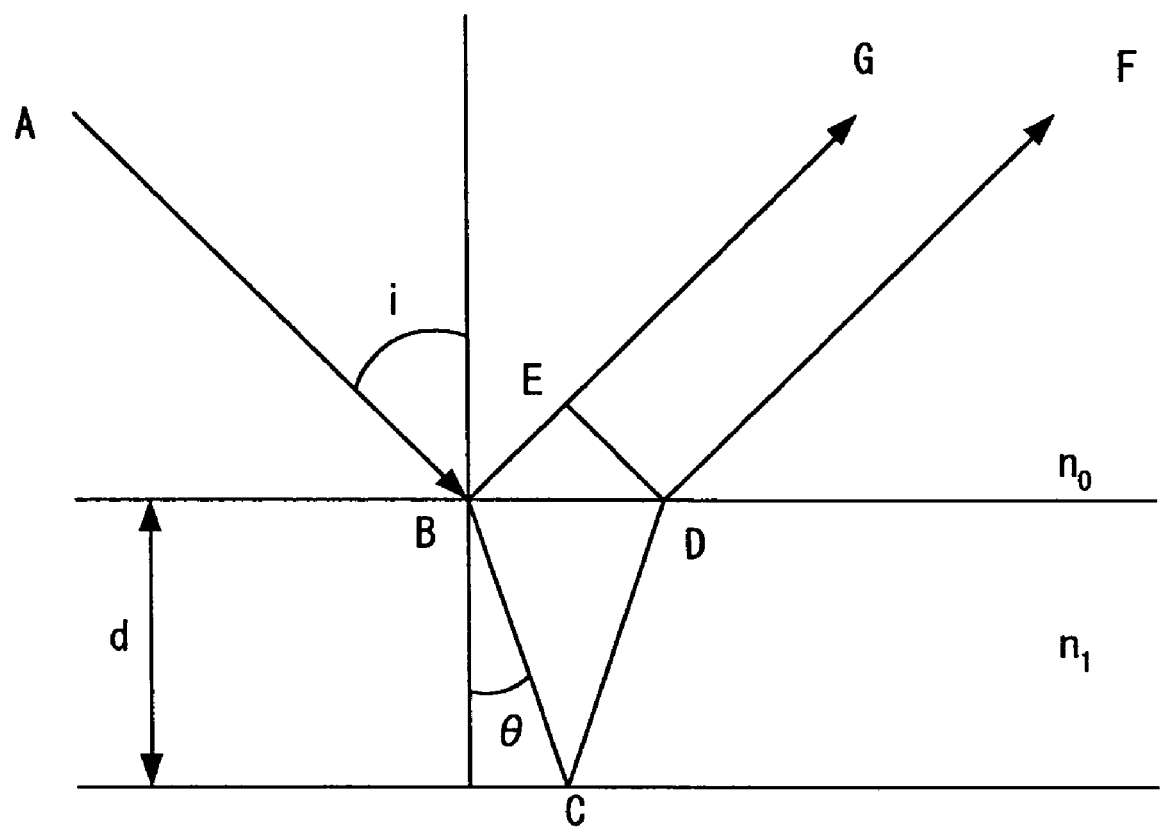
FIG. 6 is an explanatory view showing the principle of a light reflection of an incident light as colored interference light.
Figure 7:
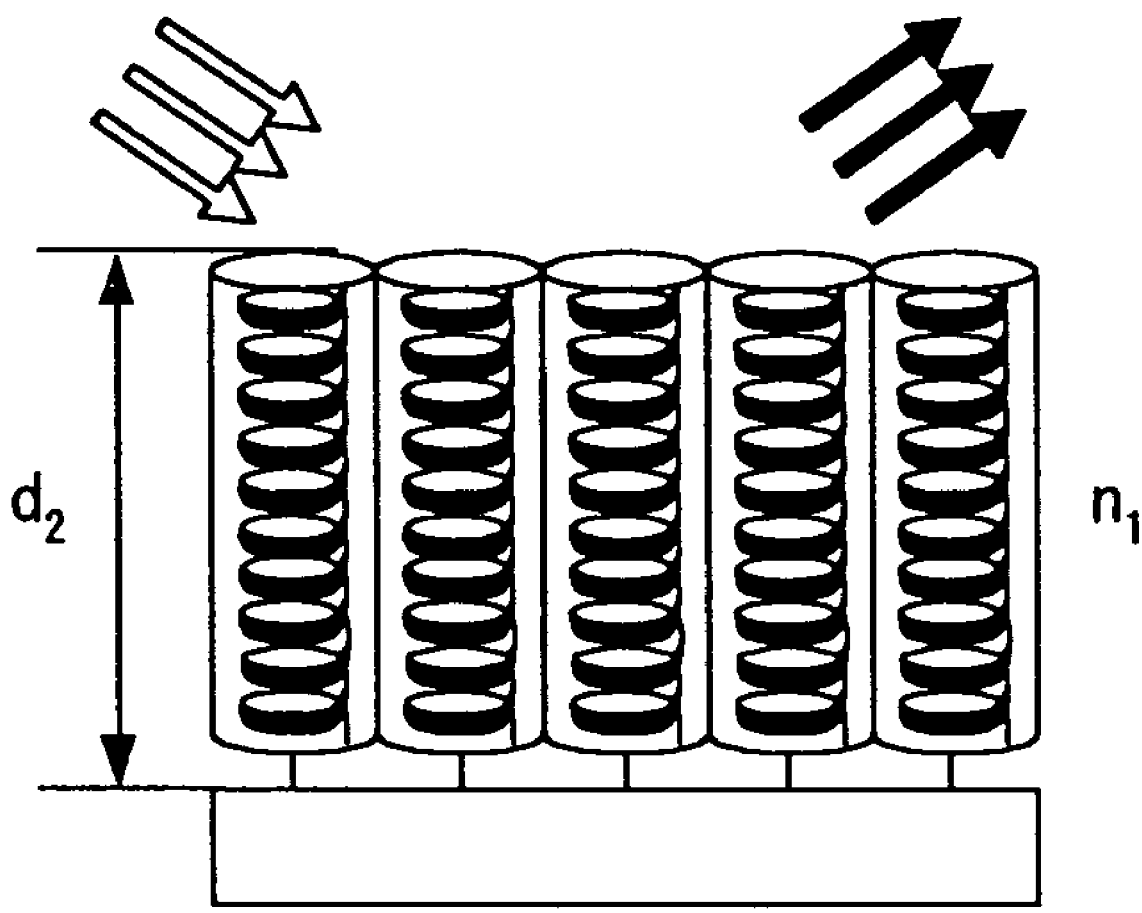
FIG. 7 is an explanatory view showing the principle of a light reflection of an incident light as colored interference light.

As shown in FIGS. 6 and 7, when a membrane consisting of rod-shaped bodies is exposed to light, the wavelength ($\lambda$) of the interference light caused by the membrane may be emphasized by condition (1) below while enfeebled by condition (2) below:

$$\lambda = \frac{2tl}{m}\sqrt{n^2 - \sin^2\alpha} \quad (1)$$

$$\lambda = \frac{4tl}{2m-1}\sqrt{n^2 - \sin^2\alpha} \quad (2)$$

In equations (1) and (2) above, $\lambda$ means the wavelength of interference light (nm), $\alpha$ means the incident angle of the light directed to the membrane, t means the thickness (nm) of the membrane, l means the number of layers in the membrane, n means the refractive index of the membrane, and m means an integer of 1 or more.

Membranes may preferably have a thickness of 810 nm or less, and more preferably 10 nm–810 nm.

The color (wavelength) may be changed by selecting the thickness of the membrane. This technique can be applied to color imaging technology.

The reflection of incident light as colored interference light may be performed by a single repeat subunit comprising a rod-shaped body and a configuration variable element, or by a linear chain consisting of two or more of such repeat subunits which are linked to another.

{Granular Substrate}

Any granular substrate that has a surface onto which a capturing unit can be fixed may be used. The size of the granules can be suitably selected depending on a particular purpose. Preferably, it may have a smaller range of particle size distribution so that it can efficiently capture its target and be post-treated easily.

The above-described granular substrate may be made of polymer such as polyacrylamide, gelatin, agar, and inorganic metals (e.g., silicon). The surface of a granular substrate may be processed, when desired, so that a capturing unit can easily be fixed to the substrate.

<Embodiments of Particle Size Variable Reactor>

One preferable embodiment of the above-described particle size (or particle diameter) variable reactor comprises a granular substrate and a capturing unit fixed onto the granular substrate in which the capturing unit has a plurality of repeat subunits each comprising a rod-shaped body, a configuration variable element attached to one end and a capturing structured body fixed to the other end of the rod-shaped body.

Figure 8:
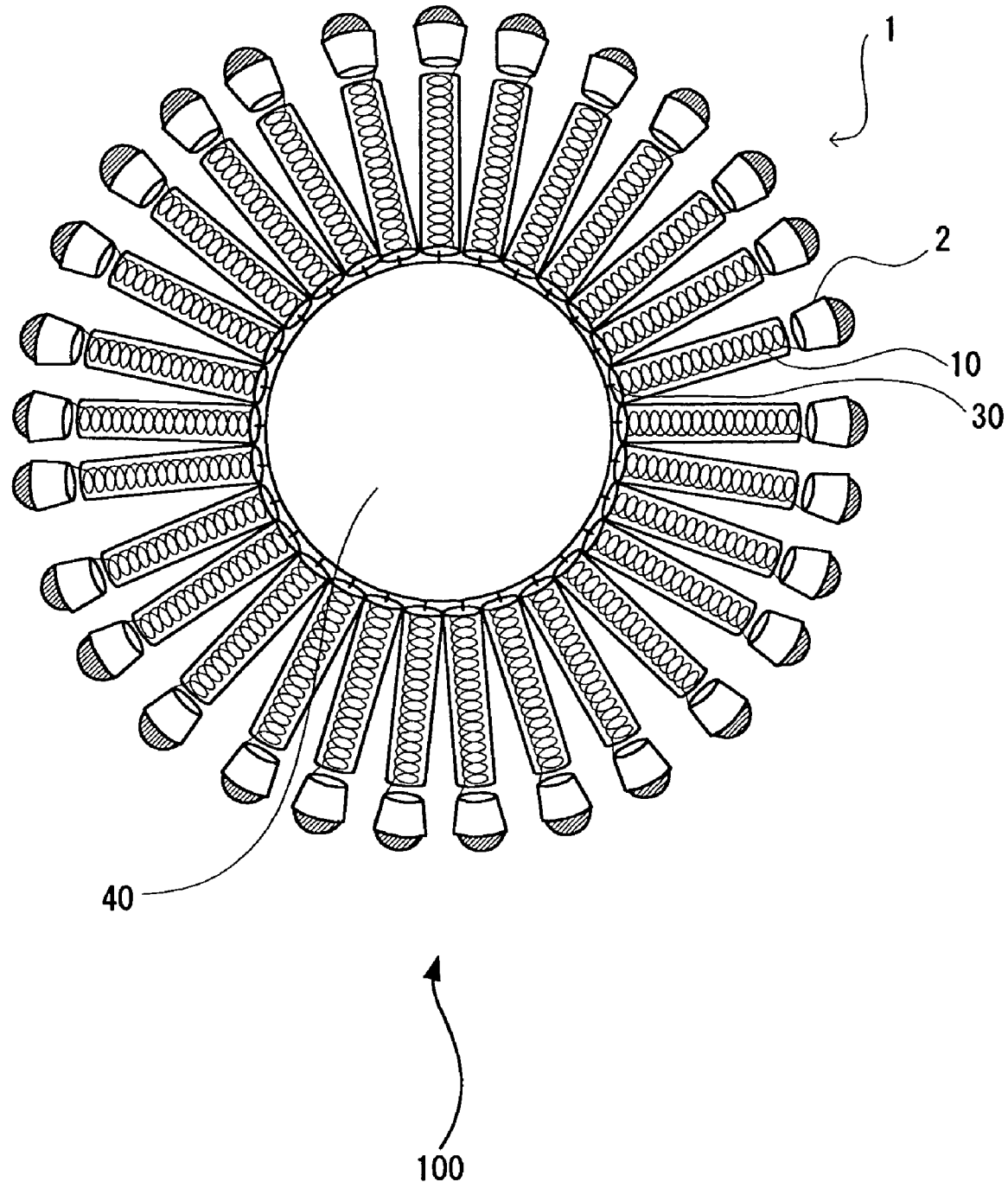
FIG. 8 is a schematic view showing one embodiment of a particle size variable reactor according to the present invention.

One preferable example of this embodiment of the above-described particle size variable reactor may be a particle size (or particle diameter) variable reactor 100 which comprises a granular substrate 40 and capturing unit 1 fixed onto the surface of the granular substrate 40 as shown in FIG. 8. In the particle size variable reactor 100, each subunit of capturing unit 1 may comprise a rod-shaped body 10, a configuration variable element 30 and a capturing structured body 2.

Figure 9A:
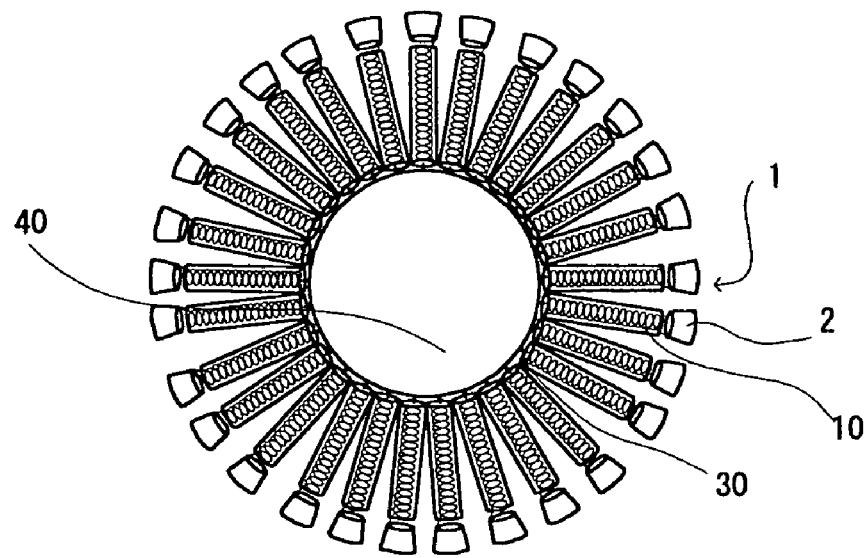
FIGS. 9A and 9B are explanatory views showing the change in the particle size of the particle size variable reactor 100 shown in FIG. 8 in which the configuration variable element 30 comprises an azobenzene compound, which can be structurally transformed by irradiation with light (UV or visible light).
Figure 9B:
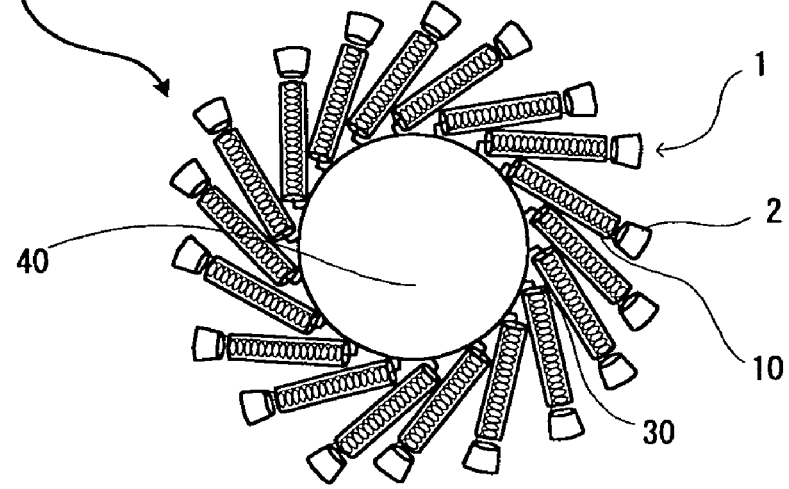

When a particle size variable reactor 100 has a configuration variable element 30 that can be structurally transformed by irradiation with light (e.g., UV or visible light), the particle size of the reactor 100 may be changed by irradiation with light (e.g., UV or visible light) as shown in FIGS. 9A and 9B.

FIGS. 9 A and B are explanatory views showing the change in the particle size of the particle size variable reactor 100 (shown in FIG. 8) which comprises an azobenzene compound as a configuration variable element 30, which can be transformed by irradiation with light (UV or visible light). The configuration variable element 30 shown in FIG.

9A is the trans-isomer of the azobenzene compound. As shown in FIG. 9 A, UV irradiation of the particle size variable reactor 100 may cause the transformation of configuration variable element 30 (azobenzene compound) from trans- to cis-isomer as described above. As a result, rod-shaped body 10 may be tilted and thus the particle size variable reactor 100 may have a reduced particle size (or particle diameter) (FIG. 9B). In this way, the particle size of the reactor 100 can be reduced by UV irradiation.

On the other hand, when the reactor 100 shown in FIG. 9B is irradiated with visible light, configuration variable elements 30 (azobenzene compound) may be transformed into trans-isomer as described above. As a result, the tilted rod-shaped body 10 may be again stood up and the reactor 100 may thus have an increased particle size (see FIG. 9A). In this way, the particle size of the reactor 100 may be increased by irradiation with visible light.

As described above, the particle size of the reactor 100 can be reversibly increased and decreased by selecting irradiation light (UV or visible light). By this configuration, the flow rate of the reactor 100 or the speed of target capturing (capturing reaction rate) can be desirably controlled. Therefore, a target can be suitably captured regardless of the type of the object to be captured, the dispersion degree of the object, capturing efficiency and the environment of the dispersion solution into which the object has been dispersed.

Figure 10:
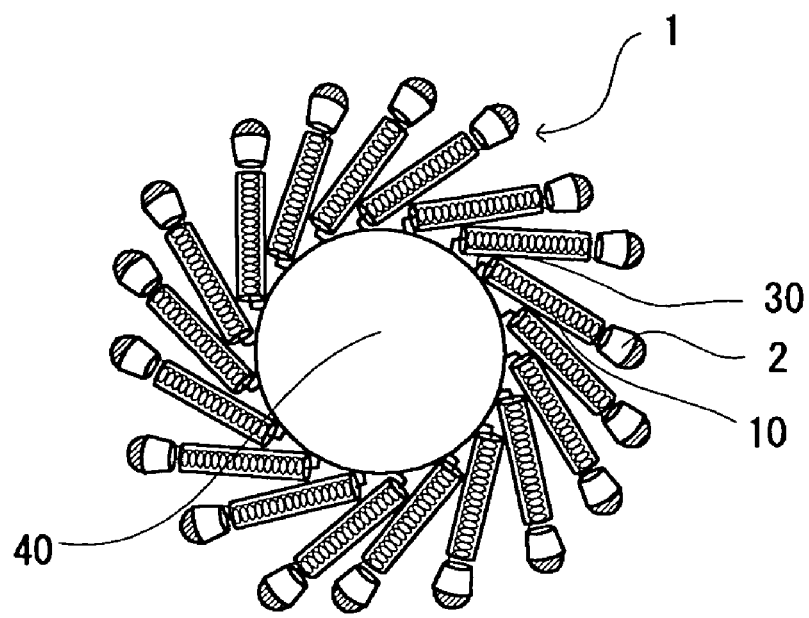
FIG. 10 is a schematic view showing exemplary particle size variable reactors according to the present invention.
Figure 10:
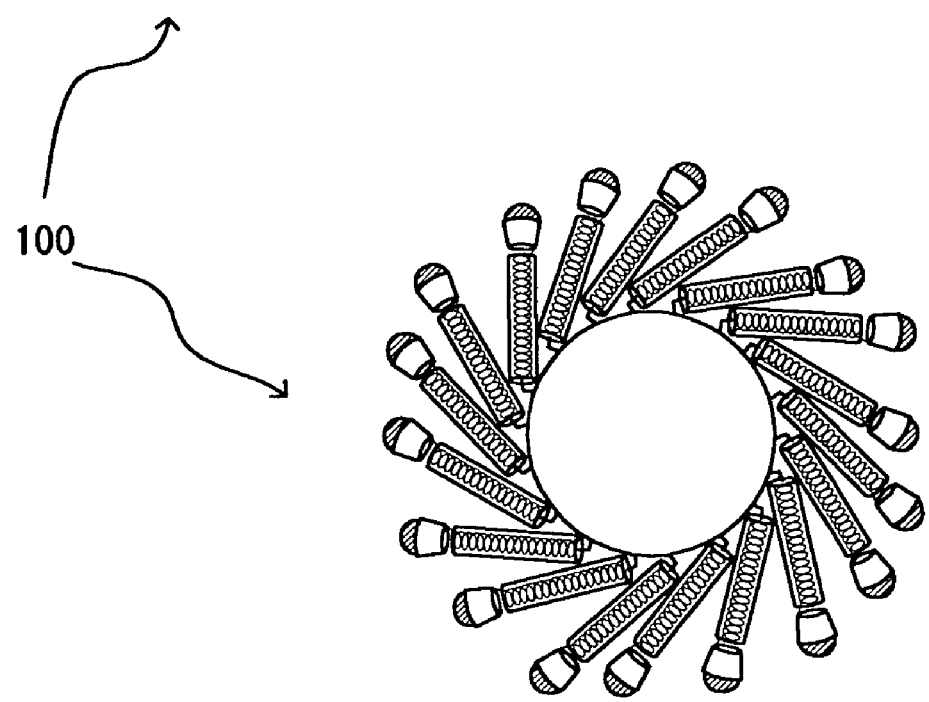

FIG. 10 shows another example of particle size variable reactor 100 in which the configuration variable element 30 comprises an azobenzene compound, with being irradiated with UV light. As described above, since configuration variable element 30 (azobenene compound) has been transformed into cis-isomer by UV irradiation, rod-shaped body 10 is tilted so that the reactor 100 has a reduced particle size. Therefore, the number of the reactor 100 that can be accommodated per unit volume may be increased and thus a higher capturing efficiency per unit volume can be obtained.

Further, a filter membrane may be preferably provided which allows the passage of a particle size variable reactor with cis-isomer of the configuration variable element (azobenzene compound) but not with trans-isomer. According to this embodiment, for example, an aqueous phase into which an object to be captured has been dispersed may be separated from an oil phase by providing such a filter membrane therebetween, whereby the object dispersed into the aqueous phase can be selectively transported into the oil phase.

Figure 11A:
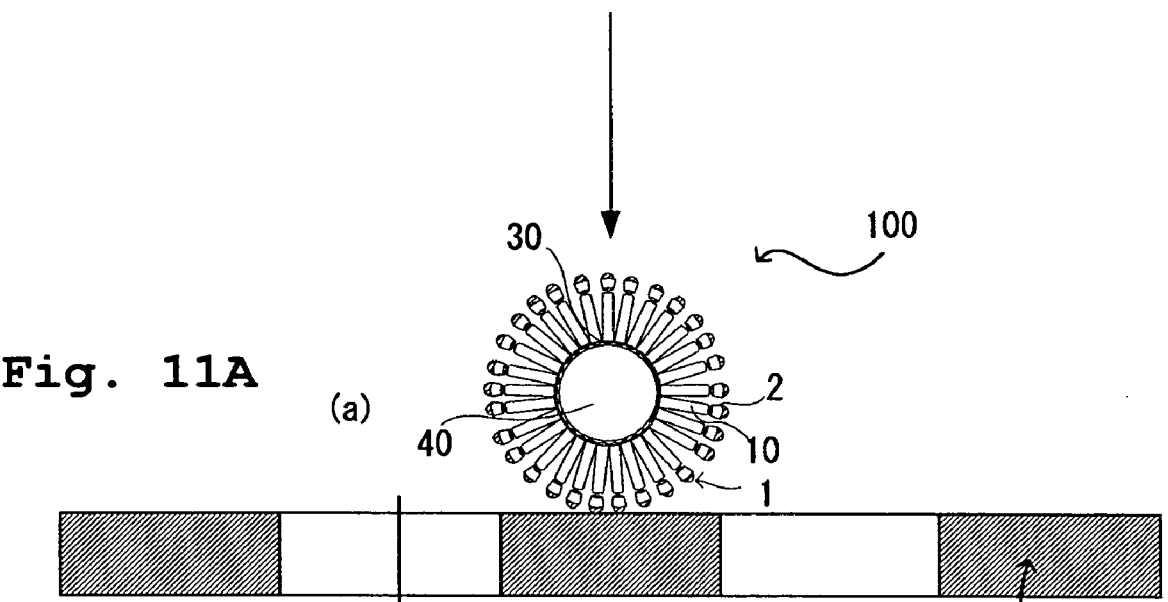
FIGS. 11A and 11B are exemplary views of particle size variable reactors 100 in which the configuration variable element 30 (azobenzene compound) is in its trans- and cis-forms, respectively.
Figure 11B:
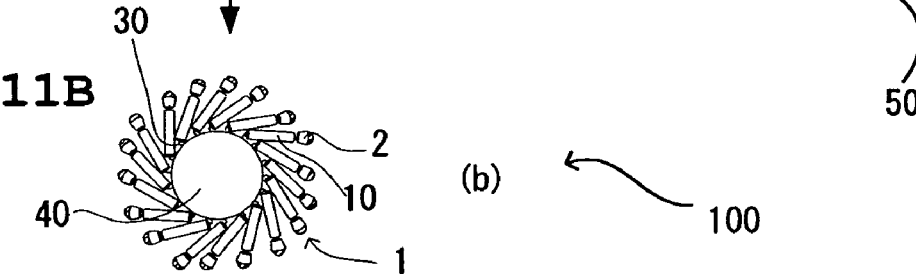

FIGS. 11A and 11B show the particle size variable reactors 100 with the configuration variable element 30 (azobenzene compound) of trans- and cis-isomers, respectively. The particle size variable reactor 100 of a larger particle size cannot pass through the filter membrane 50 as shown in FIG. 11A while one with a smaller particle size can as shown in FIG. 11B.

In FIGS. 11A and 11B, for example, when an aqueous phase into which a lipophilic target and particle size variable reactor 100 have been dispersed is separated from an oil phase by providing a filter membrane 50 therebetween in the presence of visible light irradiation, the particle size variable reactor 100 may firstly capture the object in the aqueous solution. Since the configuration variable element 30 (azobenzene compound) is present as trans-isomer, the particle size variable reactor 100 has such a larger particle size that it cannot pass through the filter membrane 50. Next, UV irradiation may convert the configuration variable element 30 (azobenzene compound) into cis-isomer. As a result, the particle size of the particle size variable reactor 100 may be reduced so that it can pass through the filter membrane 50 into the oil phase. Since the object captured by the particle size variable reactor 100 which has migrated into the oil phase is lipophilic, it may be released into the oil phase. In this way, the object may be selectively transported from the aqueous phase to the oil phase.

In the particle size variable reactor according to the present invention, the distance between the surface of the granular substrate and the capturing structured body located on the distal end of the rod-shaped body may preferably be 810 nm or less, and more preferably 350 nm–810 nm.

The particle size variable reactor according to the present invention can be preferably used in various fields including medical and industrial fields.

Examples of the present invention will be provided below though the present invention is not limited thereto.

EXAMPLE 1

—Preparation of Particle Size Variable Reactor—

Polymerization of N-carboxyl-glutamate anhydride γ-methylester (MG-NCA) is performed using β-cyclodextrin having an amino group as an initiator to obtain poly(γ-methyl L-glutamate (PMG$_{5200}$-CyD (polymerization degree: 5200)) which has β-cyclodextrin (capturing structured body) at one end of the molecule. Then, azobenzene compound is bonded to the other end (e.g., the end to which β-cyclodextrin is not attached) of the molecule of the resulting PMG$_{5200}$-CyD by any known method to obtain PMG$_{5200}$-CyD-azobenzene compound.

The poly(γ-methyl L-glutamate) has a length of 0.78 μm. Next, PMG$_{5200}$-CyD-azobenzene compound is allowed to react directly with halogenated alkyl thiol to incorporate a thiol group into PMG$_{5200}$-CyD-azobenzene compound at its azobenzene compound side. The resulting product is fixed onto a granular substrate (gold particle) having an average particle size (or diameter) per volume D$_{50}$ of 40 μm at room temperature (24° C.) to prepare a particle size variable reactor which exhibited light reflection of incident light as colored interference light.

—Capturing the Object, Irradiation with Visible or UV Light, and the Like—

Next, a solution of 2-p-toluidinylnaphthalene-6-sulfonate (TNS; SIGMA Corp.), which is the object to be captured by PMG$_{5200}$-CyD, and the particle size variable reactor obtained above in water is combined with n-hexane to form aqueous/oil phases which are partitioned by providing a filter membrane between the two phases under the conditions of visible light irradiation. After two hours, these phases are irradiated with UV light. Particle size variable reactor is detected in the oil phase. 2-p-toluidinylnaphthalene-6-sulfonate (TNS) is detected in the resulting particle size variable reactor.

The color that is structurally developed (i.e., reflected) by the particle size variable reactor when irradiated with UV light is different from that developed (i.e., reflected) by the reactor when irradiated with visible light.

In the present example, the average particle diameter per volume (D$_{50}$) of the particle size variable reactor is 40.01 μm when irradiated with UV light while it is 41.6 μm when irradiated with visible light. A filter membrane of 40.08 μm mesh diameter is used.

EXAMPLE 2

The process described in "—Preparation of particle size variable reactor—" in Example 1 was repeated except for using azomethane instead of azobenzene compound to prepare a particle size variable reactor (of which poly (γ-methyl L-glutamate) had a length of 0.78 μm), and analysis and detection were performed as described in "—Capturing the object, irradiation with visible or UV light, and others—" in Example 1 above. The same results as those obtained in Example 1 were obtained.

In the present example, the average particle diameter per volume ($D_{50}$) of the particle size variable reactor was 40.01 μm when irradiated with UV light while it was 41.6 μm when irradiated with visible light. A filter membrane of 40.08 μm mesh was used.

EXAMPLE 3

The process described in "—Preparation of particle size variable reactor—" in Example 1 above was repeated except for using azoxybenzene instead of azobenzene compound to prepare a particle size variable reactor (of which poly(γ-methyl L-glutamate) had a length of 0.78 μm), and analysis and detection were performed as described in "—Capturing the object, irradiation with visible or UV light, and others"— in Example 1 above. The same results as those obtained in Example 1 were obtained.

In the present example, the average particle diameter per volume ($D_{50}$) of the particle size variable reactor was 40.01 μm when irradiated with UV light while it was 41.6 μm when irradiated with visible light. A filter membrane of 40.08 μm mesh was used.

What is claimed is:

1. A method for selectively transporting an object from an aqueous phase to an oil phase using a particle size-variable reactor, comprising:
    providing a particle size-variable reactor that has a particle size that can be reversibly increased and decreased by light irradiation, wherein the particle size variable reactor comprises a granular substrate and a plurality of capturing units fixed onto a surface of the granular substrate, each capturing unit comprising:
    a) a capturing structured body that specifically captures the object;
    b) a configuration variable element comprising a cis-trans isomer that is reversibly transformed into a cis-isomer upon irradiation with UV light and into a trans-isomer upon irradiation with visible light; and
    c) a rod-shaped body having a length of 810 nm or less;
    providing a solution forming aqueous and oil phases that are partitioned by a filter membrane, wherein the aqueous phase contains the object to be transported;
    adding the particle size-variable reactor to the aqueous phase in the presence of visible light irradiation, such that the configuration variable element is present in the aqueous phase as the trans-isomer, and allowing the particle size variable reactor to capture the object;
    irradiating the particle size-variable reactor with UV light, thereby transforming the configuration variable element into the cis-isomer and thereby reducing the particle size of the particle size variable reactor;
    allowing the particle size-variable reactor and captured object to pass through the filter membrane, thereby selectively transporting the object from the aqueous phase to the oil phase.

2. The method according to claim 1, wherein the particle size-variable reactor reflects incident light as colored interference light.

3. The method according to claim 1, wherein the rod-shaped body is a rod-shaped organic substance.

4. The method according to claim 3, wherein the rod-shaped organic substance is selected from the group consisting of α-helix polypeptide, DNA and amylose.

5. The method according to claim 4, wherein the number of amino acids in the α-helix polypeptide is 10 to 5000.

6. The method according to claim 4, wherein the DNA comprises double-stranded DNA.

7. The method according to claim 4, wherein the amylose has an average molecular weight of 1,000 to 150,000.

8. The method according to claim 1, wherein the rod-shaped body is amphiphilic.

9. The method according to claim 2, wherein the particle size-variable reactor changes colors corresponding to a change of the colored interference light in the configuration variable element.

10. The method according to claim 1, wherein the configuration variable element is at least one compound selected from the group consisting of an azo compound and an azoxy compound.

11. The method according to claim 10, wherein the azo compound is at least one compound selected from the group consisting of an azobenzene compound, an azomethane compound, an azodicarbonamide compound and a diethyl azodicarboxylate compound.

12. The method according to claim 10, wherein the azoxy compound is at least one compound selected from the group consisting of an azoxydibenzoic acid compound and an azoxybenzene compound.

* * * * *